United States Patent [19] | [11] 4,392,489
Wagner, Sr. | [45] Jul. 12, 1983

[54] ABDUCTION PILLOW

[75] Inventor: Bill L. Wagner, Sr., Fullerton, Calif.

[73] Assignee: Bio Clinic Company, San Bernardino, Calif.

[21] Appl. No.: 283,381

[22] Filed: Jul. 15, 1981

[51] Int. Cl.³ .......................... A61F 5/37; A47G 9/00
[52] U.S. Cl. .......................... 128/80 A; 5/443
[58] Field of Search .................. 5/443, 444, 424, 437; 269/328; 128/80 A, 80 R, 133

[56] References Cited

U.S. PATENT DOCUMENTS

| | | | |
|---|---|---|---|
| 2,846,700 | 8/1958 | De Puy | 5/424 |
| 3,721,434 | 3/1973 | Spies | 5/424 |
| 3,938,205 | 2/1976 | Spann | 5/327 B |
| 3,946,451 | 3/1976 | Spann | 5/327 R |
| 4,135,504 | 1/1979 | Spann | 128/80 A |

OTHER PUBLICATIONS

Bio Clinic Company's Bio Flote Gel Products, Torso Gel Pad, Wheelchair Pads, Bio Flote Products, Bed Unit, Wheelchair Pad: Nursing and Rehabilitation Aid.

*Primary Examiner*—Alexander Grosz
*Attorney, Agent, or Firm*—Austin R. Miller

[57] ABSTRACT

Abduction apparatus includes a resilient deformable pillow having a pair of generally oppositely facing elongated exterior surfaces skew to one another with a passageway extending through the pillow in a direction generally parallel said elongated exterior surfaces, with elongated flexible binding means residing in said passageway and having length in excess of passageway length sufficiently for overlapping respective ends of said binding means about a leg of a patient contacting one of said elongated surfaces of said pillow, with pressure-sensitive fastening and receptor means at respective ends of said binding means for holding said binding means about said leg of said patient thereby laterally immobilizing said leg of said patient with respect to said pillow.

17 Claims, 3 Drawing Figures

ABDUCTION PILLOW

BACKGROUND OF THE INVENTION

1. Field of the Invention

This invention relates to abduction pillows used to immobilize legs of human patients after surgery to replace the hip joint, thereby to accelerate recovery and healing.

2. Description of the Prior Art

Abduction pillows are used to immobilize the legs of human patients after surgery to replace a hip joint, to facilitate and accelerate the healing process. Heretofore abduction pillows have been used with straps passing around the pillow and the legs of the patient, to secure the legs of the patient to the pillow thereby rendering the patient's legs substantially immovable independently of the pillow. A disadvantage with this structure is that the straps, being separate from the pillow, are easily lost and are easily soiled. This is unacceptable in a hospital environment. Additionally, separate straps sometimes allow some relative movement between the pillow and the patient's legs; this is undesirable since the patient's legs must be maintained stationary for healing to proceed.

A conventional abduction pillow is shown in the Bio Clinic Company sales bulletin entitled "Nursing and Rehabilitation Aids."

SUMMARY OF THE INVENTION

This invention provides an improved abduction pillow including a resilient deformable pillow having a pair of generally oppositely outwardly facing elongated exterior surfaces skew to one another and means for retaining legs of the human patient against the outwardly facing surfaces of the pillow so that the patient's legs are substantially laterally immovable independently of the pillow. The apparatus includes a passageway extending through the pillow, in a direction generally parallel with the elongated exterior surfaces and perpendicular to the direction of elongation thereof. Flexible binding means have length in excess of length of the passageway by an amount sufficient for overlapping respective ends thereof about a leg of a patient contacting one of the elongated exterior surfaces of the pillow. Pressure sensitive fastening and receptor means are provided for holding the binder means, upon hand application of the fastening means against the receptor means.

The binding means resides within the passageway with binding means extremities extending from either end of the passageway. The binding means preferably has an adequately large cross section that an interference fit exists between the binding means and the passageway through the pillow, with friction between the binding means and the passageway walls resisting any attempt to pull the binding means out of the passageway.

DESCRIPTION OF THE PREFERRED EMBODIMENTS

Figure 1:
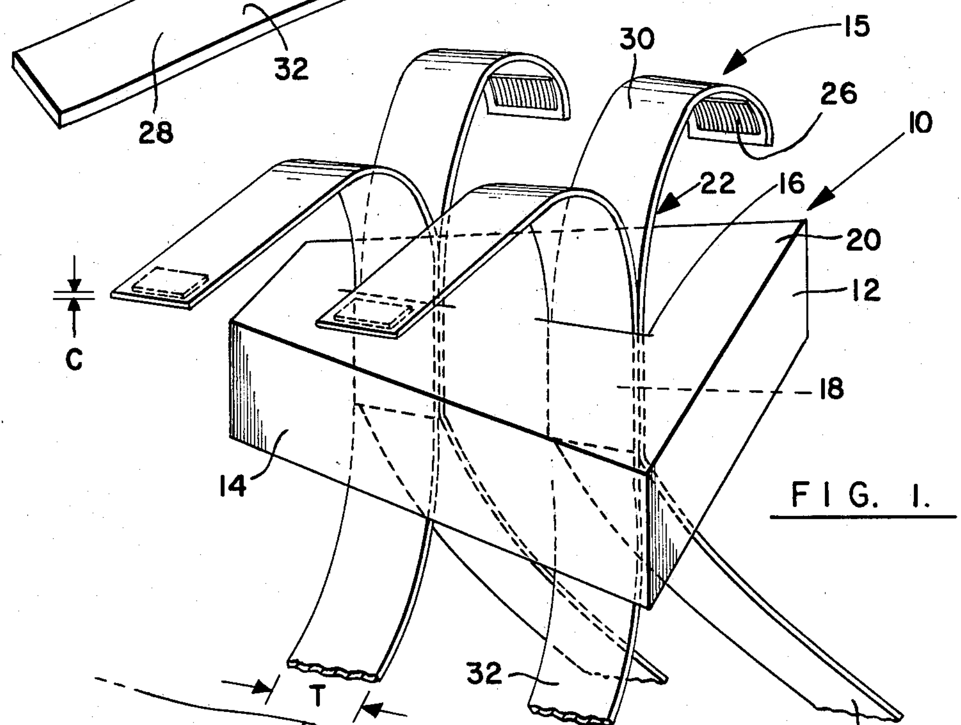
FIG. 1 is an isometric view of an abduction pillow assembly manifesting aspects of the invention.

The abduction apparatus illustrated in one preferred embodiment in FIG. 1 is designated generally 10 therein and includes a resilient deformable pillow 12 having a pair of generally oppositely facing elongated exterior surfaces 14, which are skew to one another, and means designated generally 15 for retaining individual legs of a human patient respectively against outwardly facing surfaces 14 so that the patient's legs are substantially laterally immovable independently of the abduction pillow apparatus 10.

Pillow 12 includes a passageway 18 therethrough with an orifice defining an end of passageway 18 denoted 16 in FIG. 1. Passageway 18 may be formed as a straight slit through pillow 12; passageway 18 is preferably sufficiently narrow that after the slit is formed in pillow 12, pillow material on respective sides of the slit facingly contacts. Passageway 18 extends entirely through pillow 12 from an upper surface 20 thereof to an unnumbered lower surface, not visible in FIG. 1. Passageway 18 is preferably generally parallel with elongated exterior surfaces 14 and is generally perpendicular to the direction of elongation thereof. Pillow 12 is preferably a resilient, deformable foam material and is preferably of generally truncated prismoidal configuration, as illustrated in FIG. 1, where surfaces 14 extend longitudinally and diverge one from another.

Figure 3:
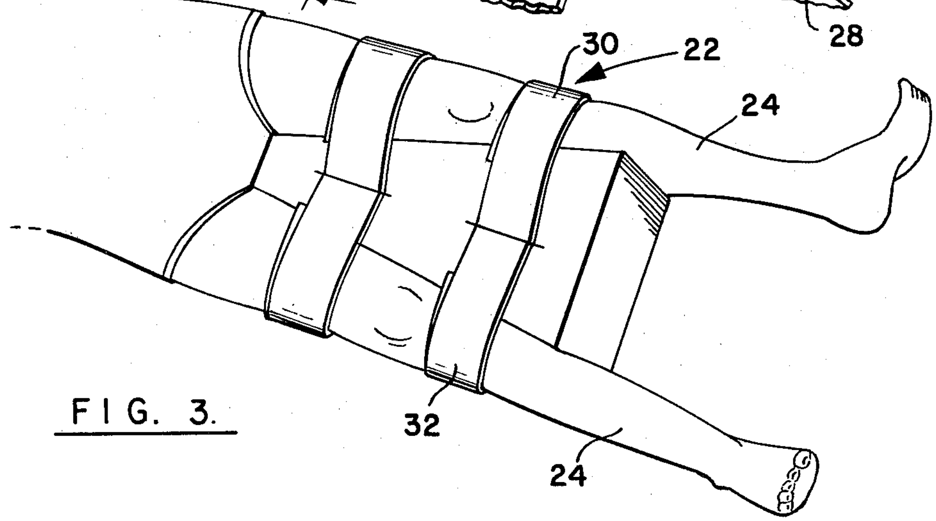
FIG. 3 illustrates the assembly of FIG. 1 used in conjunction with a human patient.

Retaining means 15 includes an elongated flexible binder 22 having length in excess of length of passageway 18 through pillow 12, with length of binder 22 exceeding length of passageway 18 sufficiently for overlapping respective ends of binder 22 around a patient's leg contacting an elongated exterior surface 14 of pillow 12; see FIG. 3 for a schematic illustration of binders 22 wrapped around legs 24 of a patient. Retaining means 15 further includes a pressure-sensitive fastening means 26 at one end of binder 22 and a receptor means 28 at an end of binder 22 remote from fastening means 26, for retaining fastening means 26 upon hand application of fastening means 26 against receptor means 28. Fastening means 26 and receptor means 28 are preferably respectively fabric hooks and either fabric eyes or fabric filaments adapted for catching the fabric hooks; suitable materials for fastening means 26 and receptor means 28 are available commercially under the trademark "Velcro."

Figure 2:
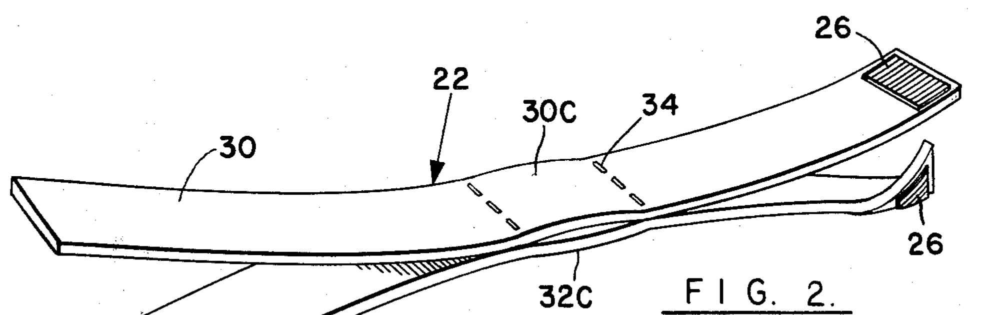
FIG. 2 is an isometric view of a binder portion of the assembly illustrated in FIG. 1.

As best shown in FIG. 2, binder 22 preferably includes two ribbon-like members 30, 32, which are preferably identical, and which are secured together in facing congruent contact one with another at central portions 30C, 32C thereof which are proximate the respective longitudinal midpoints of ribbon-like members 30, 32. Members 30,22 are preferably secured together by stitching 34 passing through fabric material from which members 30, 32 are formed in a direction generally transverse to the longitudinally extending edges of members 30, 32. Preferably two parallel lines of stitching 34 are used, spaced apart a distance less than the height C of pillow 12, which defines the length of passageway 18. With this configuration, when binder 22 is properly positioned within passageway 18, stitching 34 is within passageway 18. Stresses resulting, when binder 22 is overlapped securely about the patient's leg and fastening means 26 is pressed against receptor means 28 are not substantially transmitted to stitching 34 but are transmitted to the area of pillow material defining orifice 16.

Fastening means 26 are preferably located on the outwardly facing surfaces of members 30, 32 while receptor means 28 are preferably formed on surfaces of members 30, 32 which face one another and contact at central portions 30C, 32C. Most preferably receptor member 28 is a fabric backing extending substantially the length of members 30, 32; such construction results in the abduction pillow assembly being suited for patients of all sizes.

Cross-sectional areas and shapes of passageway 18 and binder 22 are preferably substantially identical. When passageway 18 is configured as a slit through pillow 12, preferably formed by a knife-like member being forced through pillow 12 and then removed therefrom, the cross-sectional shape of binder 22 is preferably a very elongated rectangle, as illustrated. When passageway 18 is configured as a slit and binder 32 is formed of a thin fabric material of about one-eighth inch thickness, binder 32 can be pulled through passageway 18, into position therewithin. Frictional force between binder 32 and slit-like passageway 18 retains binder 22 in place; substantial pulling is required to remove the binder from the slit.

As illustrated in FIGS. 1 and 2, it is preferable that two binders be used with a single pillow, with each binder residing within a separate passageway 16 through the pillow.

As illustrated in FIG. 3, when in use the pillow is positioned between a patient's legs with the patient's legs in facing contact with surfaces 14 of the pillow. Ribbon-like members 30, 32 of binders 22 are secured about respective legs of the patient by overlap of respective ends of ribbon-like members one with another and application of pressure to force fastening means 26 against receptor means 28. Once this has been accomplished, the patient's legs are held securely against the lateral sides of the pillow; the patient's legs are substantially immovable laterally independently of the pillow.

The abduction pillow apparatus has been fabricated with passageway 18 formed by passing a blade-like member through a flexible foam pillow 12, leaving passageway 18 configured as a thin slit with the facing surfaces of passageway 18 contacting or nearly contacting one another. Binder 22 has had ribbon-like members 32, 30 formed of flexible foam backed with a fabric receptor 28, the foam fabric receptor fabric combination being available from Smally & Bates Company sold under the trademark Velcro. When the ribbon-like members have had thickness C in FIG. 1 of about one-quarter inch and have had width T of about four inches and when slit-like passageway 18 has had width of about four and one-half inches, binder 22, when configured as shown in FIG. 2, remains within passageway 18 and resists removal therefrom with force which can be overcome by application of moderate, but not insignificant, effort by an adult.

I claim the following:

1. In abduction apparatus including a resilient deformable pillow having a pair of generally oppositely facing elongated exterior surfaces skew to one another and means for retaining a leg of a human patient respectively against one of said outwardly facing surfaces so that the patient's leg is substantially laterally immovable independently of said pillow, the improvement comprising:

a. a passageway extending through said pillow in a direction generally parallel with said elongated exterior surfaces and perpendicular to the direction of elongation thereof;

b. elongated flexible binding means extending from respective ends of the passageway and having length in excess of length of said passageway by an amount sufficient for overlapping respective ends thereof around one leg of a patient contacting one of said elongated surfaces of said pillow, and having a central portion residing slidably within and frictionally engaged by said passageway, said binding means being slidably removeable from said passageway upon application to one end of said binding means of tensile force sufficient to overcome said frictional engagement of said binding means by said passageway;

c. pressure-sensitive fastening means at one end of said binding means;

d. receptor means at an end of said binder means remote said fastening means for holding said fastening means upon hand application of said fastening means against said receptor means;

wherein said binding means is resident within said passageway with binding means extremities extending from either end thereof.

2. Apparatus of claim 1 wherein said binding means has a ribbon-like configuration.

3. Apparatus of claim 2 wherein said receptor means and said fastening means are on opposite sides of said binding means.

4. Apparatus of claim 3 wherein said receptor means covers an entire side of said binding means.

5. Apparatus of claim 4 wherein said binding means and said passageway have substantially identical cross-sectional shape and size.

6. Apparatus of claim 4 wherein said binding means and said passageway have substantially identical cross-sectional shapes.

7. Apparatus of claim 3 wherein said passageway is a slit through said pillow, with pillow material on respective sides of said slit facingly contacting when said binding means is removed from said slit.

8. Apparatus of claim 7 wherein said fastening means is a plurality of hook-like fabric structures.

9. Apparatus of claim 1 wherein said binding means fits within said passageway in an interference fit therewith.

10. Apparatus of claim 1 wherein said pillow is foam and said binding means is foam.

11. In abduction apparatus including a resilient deformable pillow having a pair of generally oppositely facing elongated exterior surfaces skew to one another and means for retaining a leg of a human patient against one of said outwardly facing surfaces so that the patient's leg is substantially laterally immovable independently of said pillow, the improvement comprising:

a. a passageway extending through said pillow in a direction generally parallel with said elongated exterior surfaces and perpendicular to the direction of elongation thereof;

b. two elongated flexible binding means having central portions secured together contiguously, said binding means extremities extending from respective ends of the passageway and having length in excess of length of said passageway by an amount sufficient for overlapping respective ends thereof around one leg of a patient contacting one of said elongated surfaces of said pillow, and having said central portions residing slidably within and frictionally engaged by said passageway, said binding means being slidably removeable from said passageway upon application to one end of said binding means of tensile force sufficient to overcome said frictional engagement of said binding means by said passageway;

c. pressure-sensitive fastening means at one end of said binding means;

d. receptor means at an end of said binder means remote said fastening means for holding said fastening means upon hand application of said fastening means against said receptor means;

wherein said binding means is resident within said passageway.

12. Apparatus of claim 11, wherein said fastening means is a plurality of hook-like fabric structures.

13. Apparatus of claim 12 wherein said receptor means is a fabric having elongated filaments for hooking thereof by said fabric hooking means.

14. Apparatus of claim 11 wherein said receptor means are on the contiguously contacting sides of said respective binding means.

15. Apparatus of claim 11 wherein said pillow and said binding means are foam.

16. Abduction apparatus including a resilient deformable foam pillow of generally truncated prismoidal configuration, having a pair of generally oppositely facing elongated exterior surfaces extending divergently from one another and means for retaining a leg of a patient respectively against one of said divergently extending outwardly facing surfaces so the patient's leg is substantially laterally immovable independently of said pillow, comprising:

a. a straight slit extending through said pillow in a direction generally parallel with said elongated exterior surfaces and perpendicular to direction of elongation thereof;

b. a longitudinally elongated flexible binder including two flexible ribbon-like members secured together in facing congruent contact one with another proximate the respective longitudinal midpoints thereof, said ribbon-like members being of length exceeding length of said passageway sufficiently for overlapping respective ends of respective ribbon-like members around respective legs of a patient contacting said respective elongated exterior surfaces of said pillow;

c. a plurality of pressure-sensitive hooking fabric fastener means at one end of each of said ribbon-like members of said binder means;

d. a plurality of pressure-sensitive fabric receptor means at ends of each of said ribbon-like members remote said hooking means, for holding said hooking means upon hand pressure application of said hooking means against said receptor means;

wherein said binder is resident within said passageway such that said facingly contacting portions of said ribbon-like members are within said passageway with said extremities of said ribbon-like members extending from either end of said passageway; wherein said hooking and receptor means are on oppositely facing surfaces of said ribbon-like members; wherein said receptor means are on surfaces of said ribbon-like members which facingly contact at the point of securement of said two ribbon-like members together.

17. Apparatus of claim 16 wherein said binder is foam.

* * * * *